US009168504B2

(12) United States Patent
Takagi et al.

(10) Patent No.: US 9,168,504 B2
(45) Date of Patent: Oct. 27, 2015

(54) FINE-PARTICLE DISPERSION LIQUID MANUFACTURING METHOD AND FINE-PARTICLE DISPERSION LIQUID MANUFACTURING APPARATUS

(75) Inventors: Tokio Takagi, Hamamatsu (JP); Mitsuo Hiramatsu, Hamamatsu (JP); Gen Takebe, Hamamatsu (JP); Naota Akikusa, Hamamatsu (JP); Kazuue Fujita, Hamamatsu (JP); Tatsuo Dougakiuchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 302 days.

(21) Appl. No.: 13/583,361

(22) PCT Filed: Mar. 10, 2011

(86) PCT No.: PCT/JP2011/055698

§ 371 (c)(1), (2), (4) Date: Oct. 1, 2012

(87) PCT Pub. No.: WO2011/111794

PCT Pub. Date: Sep. 15, 2011

(65) Prior Publication Data

US 2013/0056565 A1 Mar. 7, 2013

(30) Foreign Application Priority Data

Mar. 11, 2010 (JP) ............................... P2010-054618

(51) Int. Cl.

*B01J 13/00* (2006.01)
*B01J 19/12* (2006.01)

(Continued)

(52) U.S. Cl.

CPC ............. *B01J 19/121* (2013.01); *A61K 9/5138* (2013.01); *B01J 19/008* (2013.01); *B01J 19/128* (2013.01); *B02C 19/18* (2013.01); *B02C 23/06* (2013.01); *B02C 2019/183* (2013.01)

(58) Field of Classification Search

CPC .. B02C 19/18; B02C 2019/183; B02C 23/06; B03D 1/02; C01P 2004/61; C12N 1/066; A61K 9/5138; B01J 19/128; B01J 19/121; B01J 19/008

USPC .......................................... 241/1, 16, 21, 301

See application file for complete search history.

(56) References Cited

U.S. PATENT DOCUMENTS 5,145,684 A * 9/1992 Liversidge et al. ........... 424/489
7,597,277 B2 * 10/2009 Kawakami et al. ............... 241/1

(Continued)

FOREIGN PATENT DOCUMENTS

JP 2001-113159 4/2001
JP 2005-8524 1/2005

(Continued)

*Primary Examiner* — Faye Francis
*Assistant Examiner* — Onekki Jolly
(74) *Attorney, Agent, or Firm* — Drinker Biddle & Reath LLP

(57) ABSTRACT

A microparticle dispersion liquid manufacturing apparatus 10 includes a controller 11, a light source 12, an irradiation optical system 13, and a container 14. A solid object 1 is contained in and a solvent 2 is injected into an interior of the container 14 to enable attainment of a state where the solid object 1 is in contact with the solvent 2. The light source 12 repeatedly outputs pulsed light. By repeatedly irradiating the solvent 2 with the pulsed light from the light source 12, expansion and contraction of the solvent 2 is made to occur repeatedly at the irradiated portion, thereby generating a pressure wave in the solvent 2, and the pressure wave is made to act on the solid object 1 to finely pulverize the solid object 1 and thereby manufacture a microparticle dispersion liquid in which microparticles are dispersed in the solvent. A microparticle dispersion liquid manufacturing method and manufacturing apparatus are thereby realized by which both suppression of impurity formation and an increase in efficiency of microparticle formation can be achieved readily.

4 Claims, 15 Drawing Sheets

10

11 CONTROLLER

12 LASER LIGHT SOURCE

13

14

2

1

(51) Int. Cl.

| | |
|---|---|
| ***A61K 9/51*** | (2006.01) |
| ***B01J 19/00*** | (2006.01) |
| *B02C 19/18* | (2006.01) |
| *B02C 23/06* | (2006.01) |

(56) References Cited

U.S. PATENT DOCUMENTS

| | | | | |
|---|---|---|---|---|
| 7,597,278 | B2 * | 10/2009 | Asahi et al. | 241/1 |
| 2006/0257489 | A1 * | 11/2006 | Kawakami et al. | 424/489 |
| 2007/0152360 | A1 * | 7/2007 | Kawakami et al. | 264/5 |
| 2009/0081301 | A1 * | 3/2009 | Takebe et al. | 424/489 |

FOREIGN PATENT DOCUMENTS

| | | |
|---|---|---|
| JP | 2009-79007 | 4/2009 |
| JP | 2009-84249 | 4/2009 |
| JP | 4398182 | 1/2010 |
| WO | 2007/116632 | 10/2007 |
| WO | 2007/132852 | 11/2007 |

* cited by examiner

*Fig.6*

| WATER INJECTION AMOUNT (mL) | SUCCESS/FAILURE OF FINE PULVERIZATION AFTER 1 MINUTE OF LASER LIGHT IRRADIATION |
|---|---|
| 0 | × |
| 0.1 | ○ |
| 0.2 | ○ |
| 0.3 | ○ |
| 0.4 | ○ |
| 0.5 | ○ |
| 0.6 | ○ |
| 0.7 | × |
| 0.8 | × |
| 0.9 | × |
| 1.0 | × |

Fig.7

| CONDITION | PULSE WIDTH, REPETITION FREQUENCY | Duty | AVERAGE OUTPUT | PEAK OUTPUT | IRRADIATION TIME |
|---|---|---|---|---|---|
| (A) | 100ns, 100kHz | 1% | 31mW | 3.1W | 10 MINUTES |
| (B) | 100ns, 500kHz | 5% | 155mW | 3.1W | 10 MINUTES |
| (C) | 500ns, 100kHz | 5% | 155mW | 3.1W | 10 MINUTES |
| (D) | 500ns, 500kHz | 25% | 775mW | 3.1W | 10 MINUTES |

| Data Item | Value |
| --- | --- |
| MV (μm) | 0.1404 |
| MN (μm) | 0.1041 |
| MA (μm) | 0.1275 |
| CS | 47.073 |
| SD (μm) | 0.0427 |

| Peak (μm) | Vol (%) | Width (μm) |
| --- | --- | --- |
| 0.1373 | 100.00 | 0.0853 |
| | | |
| | | |
| | | |
| | | |
| | | |

| Data Item | Value |
|---|---|
| MV (μm) | 0.2023 |
| MN (μm) | 0.1535 |
| MA (μm) | 0.1854 |
| CS | 32.357 |
| SD (μm) | 0.0588 |

| Peak (μm) | Vol (%) | Width (μm) |
|---|---|---|
| 0.1984 | 100.00 | 0.1176 |
| | | |
| | | |
| | | |
| | | |
| | | |

*Fig.12*

| WATER ADDED AMOUNT (mL) | SUCCESS/FAILURE OF FINE PULVERIZATION AFTER 1 MINUTE OF LASER IRRADIATION |
|---|---|
| 0 | × |
| 0.1 | ○ |
| 0.2 | ○ |
| 0.3 | ○ |
| 0.4 | ○ |
| 0.5 | ○ |
| 0.6 | × |
| 0.7 | × |
| 0.8 | × |
| 0.9 | × |
| 1.0 | × |

FINE-PARTICLE DISPERSION LIQUID MANUFACTURING METHOD AND FINE-PARTICLE DISPERSION LIQUID MANUFACTURING APPARATUS

TECHNICAL FIELD

The present invention relates to a method and an apparatus for manufacturing a microparticle dispersion liquid.

BACKGROUND ART

In the recent development of new medical drugs, combinatorial chemistry methods have been adopted in synthesizing candidate compounds. Combinatorial chemistry is the art of adopting combinations to synthesize a wide variety of compounds in a short time at one time. Compounds obtained by this method have a solubility problem in many cases. That is, in many cases, even if a compound is found to have excellent physiological activity in itself, if the compound has a property of being difficult to dissolve in water, development of the compound is abandoned. Even with compounds obtained by extraction from natural products, various organic syntheses are carried out and structural optimization is performed to improve solubility. Some medical drugs already on the market are also low in solubility. With such drugs, a medicament absorption amount varies within an individual patient and varies among individuals, and this places a large burden in terms of control of levels in blood, etc., on both a physician using a drug and a patient on whom the drug is used.

Microparticle formulations have received attention as a solution to the above problems. With a microparticle formulation, poorly-soluble medicament particles that are made no more than a micrometer in size are dispersed in water with stability. By using a microparticle formulation, a medicament can be increased in absorption rate and amount in a living body. Reduction in variation of absorption amount within an individual patient and among individuals and increase in effective availability with respect to a dose can also be anticipated. Inventions of methods for manufacturing such microparticle formulations are disclosed in Patent Documents 1 and 2.

With the invention disclosed in Patent Document 1, in order to finely pulverize a solid object, which is suspended in a solvent of a treatment target liquid without being dissolved, and thereby manufacture microparticles of the solid object, the treatment target liquid is irradiated with light of a predetermined wavelength, which is longer than an absorption band of the solid object, is in an absorption band of the solvent, and is absorbed by the solvent, to finely pulverize the solid object, and an irradiation intensity of the light irradiated on the treatment target liquid is made lower than an irradiation light intensity at which two-photon absorption occurs in the solid object.

With the invention disclosed in Patent Document 2, a solid object is finely pulverized by injecting water into an interior of a container in which the solid object is fixed to an inner wall and irradiating the solid object fixed to the inner wall of the container with light. In irradiation with the light, the light is irradiated from outside a region of the inner wall of the container at which the solid object is fixed to make the irradiated light propagate in the order of the container, the solid object, and the water so that microparticles can be formed at a fixed efficiency without lowering of efficiency of microparticle formation even in a state where the water contains a high concentration of microparticles.

CITATION LIST

Patent Literature

Patent Document 1: Japanese Patent Publication No. 4398182

Patent Document 2: International Publication WO 2007/116632

SUMMARY OF INVENTION

Technical Problem

When a solid object is irradiated with light, depending on a wavelength or an intensity of the irradiated light, a photochemical reaction may occur via an electronically excited state in the solid object that absorbs the irradiated light and an unintended impurity may thereby be formed. It is important to avoid the formation of an unintended impurity in a case where the microparticles to be manufactured is a medical drug.

Thus, with the inventions disclosed in Patent Documents 1 and 2, the wavelength and intensity of the irradiated light must be set so that an impurity is not formed. Thus, with the inventions disclosed in Patent Documents 1 and 2, there is a limit to increasing the efficiency of microparticle formation and suppression of impurity formation and an increase in microparticle formation efficiency cannot be realized readily at the same time.

The present invention has been made to resolve the above problem, and an object thereof is to provide a microparticle dispersion liquid manufacturing method and a microparticle dispersion liquid manufacturing apparatus by which both suppression of impurity formation and an increase in microparticle formation efficiency can be realized readily.

Solution to Problem

A method for manufacturing a microparticle dispersion liquid according to the present invention includes (1) an injecting step of injecting a solvent into a container containing a solid object to attain a state where the solid object is in contact with the solvent inside the container, and (2) an irradiating step of performing, after the injecting step, repeated irradiation on the solvent with pulsed light selectively among the solid object and the solvent inside the container to cause expansion and contraction of the solvent to occur repeatedly at the irradiated portion to generate a pressure wave in the solvent and make the pressure wave act on the solid object to finely pulverize the solid object and thereby manufacture the microparticle dispersion liquid in which microparticles are dispersed in the solvent.

The above-described microparticle dispersion liquid manufacturing method preferably further includes (3) a dissolving step of dissolving a poorly-soluble medicament and a dispersion stabilizer in a volatile organic solvent and (4) a fixing step of performing elimination by evaporation of the organic solvent, contained in a solution obtained in the dissolving step, and fixing the solid object, obtained by the organic solvent elimination, on an inner wall of the container, and preferably, the injecting step and the irradiating step are performed after performing the fixing step.

In the manufacturing method described above, a single container may be used throughout the entirety of the dissolving step, fixing step, injecting step, and irradiating step. The container used in the steps until the solid object is obtained and the container used in the steps from the fixing of the solid object onward may be separate from each other.

A microparticle dispersion liquid manufacturing apparatus according to the present invention includes (1) a container, in an interior of which a solid object is contained and a solvent is injected to attain a state where the solid object is in contact with the solvent, and (2) a light source repeatedly irradiating the solvent with pulsed light selectively among the solid object and solvent inside the container. Further, in the microparticle dispersion liquid manufacturing apparatus according to the present invention, the repeated irradiation of the solvent with the pulsed light from the light source causes expansion and contraction of the solvent to occur repeatedly at the irradiated portion, thereby generating a pressure wave in the solvent, and the pressure wave is made to act on the solid object to finely pulverize the solid object and thereby manufacture a microparticle dispersion liquid in which microparticles are dispersed in the solvent.

In the above-described microparticle dispersion liquid manufacturing apparatus, preferably, a poorly-soluble medicament and a dispersion stabilizer are dissolved in a volatile organic solvent in the interior of the container, the solid object obtained by elimination by evaporation of the organic solvent contained in the solution is fixed to an inner wall of the container, and the solvent is injected into the interior of the container. In this case, injection of the solvent into the container and pulsed light irradiation on the solvent are performed thereafter.

Advantageous Effects of Invention

According to the present invention, both suppression of impurity formation and an increase in efficiency of microparticle formation can be achieved readily.

BRIEF DESCRIPTION OF DRAWINGS

FIG. 6 is a table summarizing success/failure of fine pulverization at various values of amount of water as a solvent injected in a well in Example 1.

FIG. 7 is a table summarizing output conditions of pulsed laser light in Example 2.

FIG. 12 is a table summarizing success/failure of fine pulverization at various values of amount of water as a solvent injected in a well under the condition (A) in Example 2.

DESCRIPTION OF EMBODIMENTS

Hereinafter, embodiments for carrying out the present invention will be described in detail with reference to the attached drawings. In the description of the drawings, the same components will be provided with the same reference symbols, and overlapping description will be omitted.

Figure 1:
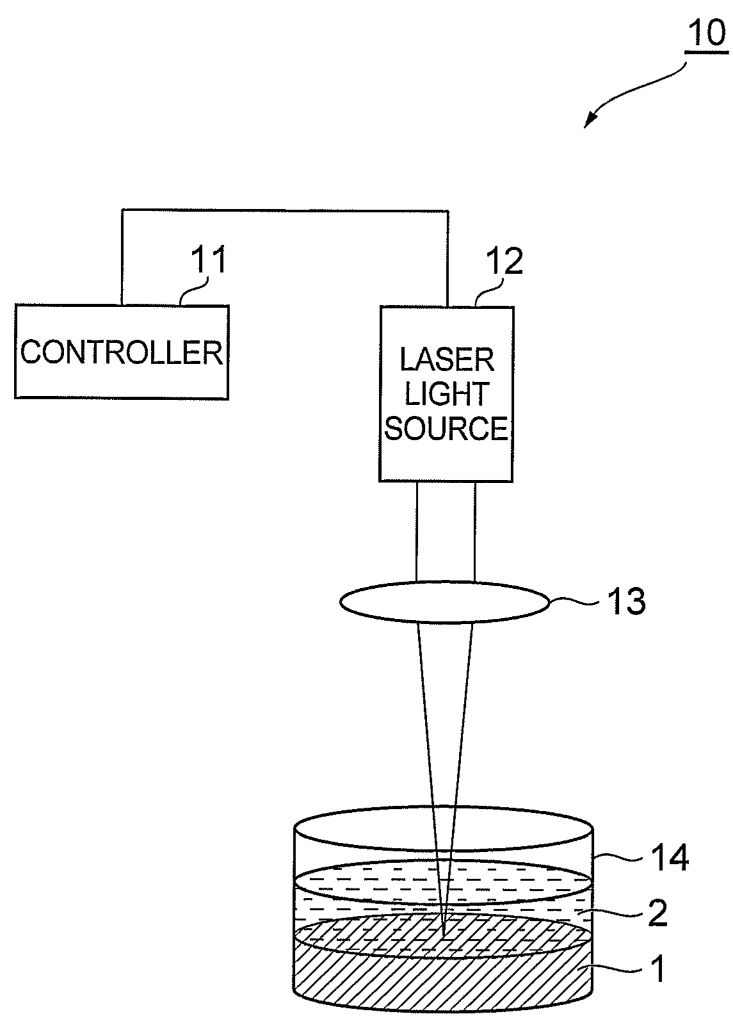
FIG. 1 is a configuration diagram of a microparticle dispersion liquid manufacturing apparatus 10 according to an embodiment.

FIG. 1 is a configuration diagram of a microparticle dispersion liquid manufacturing apparatus 10 according to an embodiment. The microparticle dispersion liquid manufacturing apparatus 10 according to the present embodiment includes a controller 11, a light source 12, an irradiation optical system 13, and a container 14 and finely pulverizes a solid object 1 inside the container 14 to manufacture a microparticle dispersion liquid in which the microparticles are dispersed in a solvent 2.

The container 14 may be put in a state where the solid object 1 is in contact with the solvent 2 by the solid object 1 being contained in an interior thereof and the solvent 2 being injected into the interior thereof. For example, a multi-well plate having a plurality of wells formed in a plate in common is preferably used, and in this case, each individual well is used as the container 14. The container 14 may be made of any material and, for example, may be made of polypropylene.

The light source 12 outputs a pulsed light beam repeatedly. The light source 12 is preferably a pulsed laser light source. A wavelength of the pulsed laser light output from the light source 12 is preferably included in a wavelength range in which an absorption coefficient of the solvent 2 injected into the container 14 is large. Also, the light source 12 may be a solid-state laser light source or may be a semiconductor laser light source, and in the latter case, may be a quantum cascade laser light source. In a case where a plurality of the containers 14 are used as in the case of using a multi-well plate, a semiconductor laser array in which a plurality of semiconductor laser light sources are disposed in parallel is preferably used.

The irradiation optical system 13 guides the pulsed laser light output from the light source 12, and repeatedly irradiates the solvent 2 with the pulsed laser light selectively among the solid object 1 and the solvent 2 inside the container 14. The irradiation optical system 13 is preferably a condensing optical system that condenses and irradiates the pulsed laser light into the solvent 2. Also, the irradiation optical system 13 preferably includes a scanning unit that scans an irradiating position of the pulsed laser light.

When as illustrated, the solvent 2 is present above and in contact with the solid object 1 in the interior of the container 14 having an opening at an upper portion, the light source 12 that outputs pulsed laser light of a wavelength at which the absorption coefficient of the solvent 2 is high may be used, and the solvent 2 may be irradiated with the pulsed laser light from above by the irradiation optical system 13. In this case, most of the energy of the pulsed laser light is absorbed by the solvent 2 and the energy of the pulsed laser light arriving at the solid object 1 is made slight so that photodegradation and thermal degradation of the solid object 1 are suppressed.

The controller 11 controls operation of the light source 12. Specifically, the controller 11 performs control of start and stop of the repeated output of the pulsed laser light from the light source 12 and also performs control of power, pulse width, and repetition frequency of the pulsed laser light output from the light source 12. In a case where the light source 12 is variable in output wavelength, the controller 11 preferably also controls the output wavelength of the light source 12.

The microparticle dispersion liquid manufacturing apparatus 10 may further include a temperature adjusting part including a constant temperature reservoir, a thermometer, and a temperature control unit. In this case, the container 14 housed inside the constant temperature reservoir and the treatment target liquid contained in the interior of the container 14 are maintained at a fixed temperature by feedback control by the thermometer and the temperature control unit. A portion of the constant temperature reservoir, through which the pulsed laser light output from the light source 12 passes, is configured as a transparent window.

Figure 2:
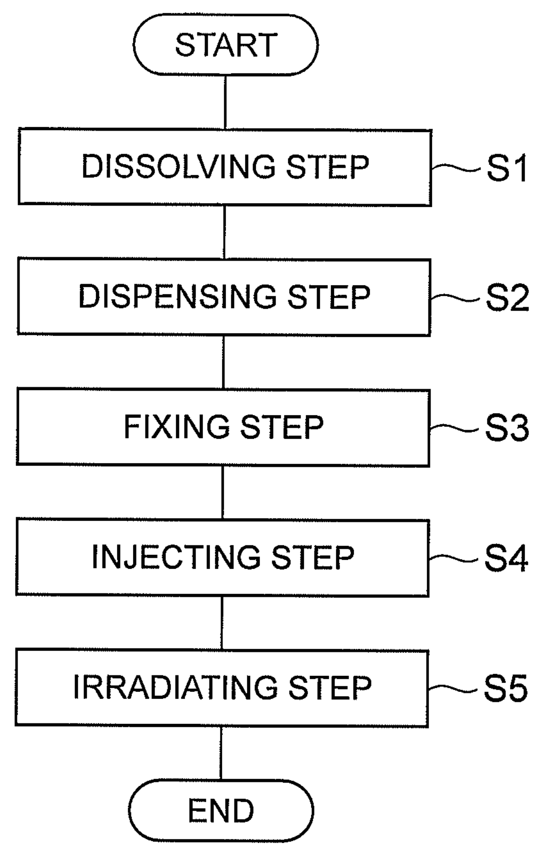
FIG. 2 is a flowchart for describing a microparticle dispersion liquid manufacturing method according to the embodiment.

An example of operation of the microparticle dispersion liquid manufacturing apparatus 10 according to the present embodiment shall now be described along with a microparticle dispersion liquid manufacturing method according to the present embodiment. FIG. 2 is a flowchart for describing the microparticle dispersion liquid manufacturing method according to the present embodiment. In the microparticle dispersion liquid manufacturing method according to the present embodiment described below, a multi-well plate is used as the container 14 and a liquid in which microparticles, including a poorly-soluble medicament and a dispersion stabilizer, is dispersed in water is manufactured by successively performing a dissolving step S1, a dispensing step S2, a fixing step S3, an injecting step S4, and an irradiating step S5.

In the dissolving step S1, the poorly-soluble medicament and the dispersion stabilizer are dissolved in a volatile organic solvent inside the container 14. Here, the poorly-soluble medicament is a medicament that hardly dissolves in water and although solubility thereof is not restricted in particular, the solubility is preferably no more than 50 μg/mL at a temperature of 25° C. Commercially available drugs, such as cyclosporin, tacrolimus, nifedipine, nicardipine hydrochloride, phenytoin, digitoxin, diazepam, nitrofurantoin, benoxaprofen, griseofulvin, sulfathiazole, piroxicam, carbamazepine, phenacetin, tolbutamide, theophylline, griseofulvin, chloramphenicol, paclitaxel, camptothecin, cisplatin, daunorubicin, methotrexate, mitomycin C, docetaxel, vincristine, amphotericin B, nystatin, and clobetasone butyrate and other corticosteroids, and other new drug candidate compounds in development can be cited as examples of the poorly-soluble medicament.

The dispersion stabilizer is preferably a high molecular polymer or a surfactant. The high molecular polymer is preferably a substance that is high in water solubility and is readily soluble in various organic solvents. Hydroxypropyl methylcellulose, methylcellulose, hydroxypropyl cellulose, hydroxypropyl methylcellulose phthalate, hydroxypropyl methylcellulose acetate succinate, carboxymethylcellulose sodium, cellulose acetate phthalate, and other cellulose derivatives, agar, gelatin, sodium alginate, polyvinylpyrrolidone, aminoalkylmethacrylate copolymer, methacrylic acid copolymer, carboxyvinyl polymer, polyvinyl alcohol, polyethylene glycol, etc., can be cited as examples of the high molecular polymer. The surfactant is preferably of low toxicity, and sodium lauryl sulfate, cholic acid, deoxycholic acid, polyoxyethylene sorbitan fatty acid ester, etc., can be cited as examples.

As the organic solvent, methanol, ethanol, propanol, and other alcohols, acetone, acetonitrile, methyl acetate, ethyl acetate, diethyl ether, etc., can be cited as examples, and methanol, ethanol, propanol, and other alcohols are more preferable.

In the dispensing step S2 following the dissolving step S1, the solution obtained in the dissolving step S1 is dispensed equally in the respective wells of the multi-well plate used as the containers 14. In the fixing step S3 following the dispensing step S2, the organic solvent contained in the solutions dispensed in the respective containers 14 in the dispensing step S2 is eliminated by evaporation, and by the organic solvent elimination, pellet-form solid objects 1 are obtained and the solid objects 1 are fixed to bottom portions of the containers 14.

In the injecting step S4 following the fixing step S3, water is injected as the solvent 2 into the interiors of the containers 14. By the injection, the solid object 1 fixed to the bottom portion of each container 14 is immersed in the solvent 2 (see FIG. 1). Then, in the irradiating step S5 following the injecting step S4, the pulsed laser light that is output from the light source 12 and has passed through the irradiation optical system 13 is irradiated from above onto the solvent 2 inside the container 14 and most of the energy is absorbed by the solvent 2.

By the solvent 2 being irradiated with the pulsed laser light in the irradiating step S5, although the light energy absorbed by the solvent at the irradiated portion is converted into heat energy to cause rapid thermal expansion and evaporation of the solvent at the irradiated portion, the solvent at the irradiated portion is immediately cooled thereafter by the surrounding solvent to cause contraction and condensation of the solvent at the irradiated portion. That is, by the solvent 2 being repeatedly irradiated with the pulsed laser light, expansion and contraction of the solvent 2 occur repeatedly at the irradiated portion and a pressure wave is generated in the solvent 2. The pressure wave propagates through the solvent 2 and arrives at a surface of the solid object 1 to act on the solid object 1 and finely pulverizes the solid object 1. A microparticle dispersion liquid, in which the microparticles are dispersed in the solvent 2, is thereby manufactured. The microparticles include the poorly-soluble drug and the dispersion stabilizer.

Microparticles, including the poorly-soluble medicament and the dispersion stabilizer, are manufactured from the microparticle dispersion liquid manufactured as described above. Or, lyophilized microparticles are manufactured by lyophilizing the microparticle dispersion liquid. Furthermore, an oral administration formulation, containing the microparticle dispersion liquid, the microparticles, or the lyophilized microparticles, is manufactured, or an injection formulation, containing a dispersion liquid, obtained by resuspending the microparticle dispersion liquid, the microparticles, or the lyophilized microparticles in water, is manufactured.

Thus, with the microparticle dispersion liquid manufacturing apparatus 10 according to the present embodiment or the microparticle dispersion liquid manufacturing method according to the present embodiment, pulsed laser light is repeatedly irradiated selectively on the solvent 2 among the solid object 1 and the solvent 2, the pressure wave due to repeated expansion and contraction of the solvent 2 is generated in the solvent 2 at the irradiated portion, and the solid object 1 is finely pulverized by the pressure wave acting on the solid object 1. Light energy or heat energy thus does not act directly on the solid object 1.

A degree of freedom of selection of the wavelength or intensity of the pulsed laser light is thus high and both suppression of impurity formation from the solid object 1 and an increase in efficiency of the microparticle formation can be achieved readily. The microparticle dispersion liquid manufacturing apparatus 10 according to the present embodiment or the microparticle dispersion liquid manufacturing method according to the present embodiment may be used especially favorably in a case where the microparticles to be manufactured are those of a medical drug.

Also, with the microparticle dispersion liquid manufacturing apparatus 10 according to the present embodiment, a semiconductor laser light source may be used as the light source 12, thereby enabling a reduction in size and saving of electric power, and also, control of the output intensity, repetition frequency, etc., of the pulsed laser light is easy and fine pulverization can thus be performed under various conditions. Further, with the microparticle dispersion liquid manufacturing apparatus 10 according to the present embodiment, a multi-well plate may be used as the container 14, a semiconductor laser array may be used as the light source 12, and processing efficiency of fine pulverization can thus be improved readily.

(Example 1)

Specific examples of the microparticle dispersion liquid manufacturing apparatus or the microparticle dispersion liquid manufacturing method according to the embodiment shall now be described.

First, Example 1 shall be described. In Example 1, a microparticle dispersion liquid of an immunosuppressant, Cyclosporin A (hereinafter referred to as "CsA"), which is a poorly-soluble medicament, was prepared. CsA bulk powder (1 g) as the poorly-soluble medicament and polyvinylpyrrolidone (5 g) and sodium lauryl sulfate (200 mg) as dispersion stabilizers were placed in a test tube and dissolved in ethanol (100 mL), which is a volatile organic solvent.

After dispensing of the solution (3 mL) into each well portion of a 24-well multi-well plate, the ethanol was dried in an oven heated to a temperature of 60° C. to obtain solid objects, which are mixtures of the medicament and the dispersion stabilizers, at the bottom portions of the respective wells. Water (0.2 mL) was then injected as the solvent into each well containing the solid object. Each well had a bottom surface area of 1.88 $cm^2$ and thus a layer of approximately 1 mm depth was formed with the water.

The water layer inside the well was repeatedly irradiated with pulsed laser light output from a quantum cascade laser light source from above the well. The pulsed laser light had a wavelength of 8.6 μm, an average output of 120 mW, a peak output of 10 W, a pulse width of 120 ns, and a repetition frequency of 100 kHz.

Further, a near infrared range lens with a focal length of 50 mm was used as the irradiation optical system to condense the pulsed laser light near a surface of the water layer. A light condensed portion had an elliptical spot shape with a major diameter of 2 mm and a minor diameter of 1 mm. The laser fluence was 76 $\mu J/cm^2$. The light condensed portion became cloudy 10 seconds after start of irradiation. A microparticle dispersion liquid of CsA was obtained by taking out just the cloudy water layer portion by a micropipette. In the present example, all of the above procedures were performed at room temperature (20° C.).

The amount and purity of CsA contained in the dispersion liquid obtained were quantified by measuring absorbance at 210 nm wavelength using high performance liquid chromatography (hereinafter referred to as "HPLC"). ODS-C18 (manufactured by Tosoh Corporation) was used as a separation carrier, and acetonitrile-isopropanol-water (55:15:30) was used as a mobile phase to make measurements at a flow velocity of 1 mL/min and a temperature of 60° C. The dispersion liquid obtained was diluted by 10 times by methanol-water (1:1) and subject to measurement after the microparticles were dissolved completely. A solution, prepared by dissolving CsA bulk powder in methanol-water (1:1) to a concentration of 1 mg/mL, was used as a reference preparation.

Figure 3:
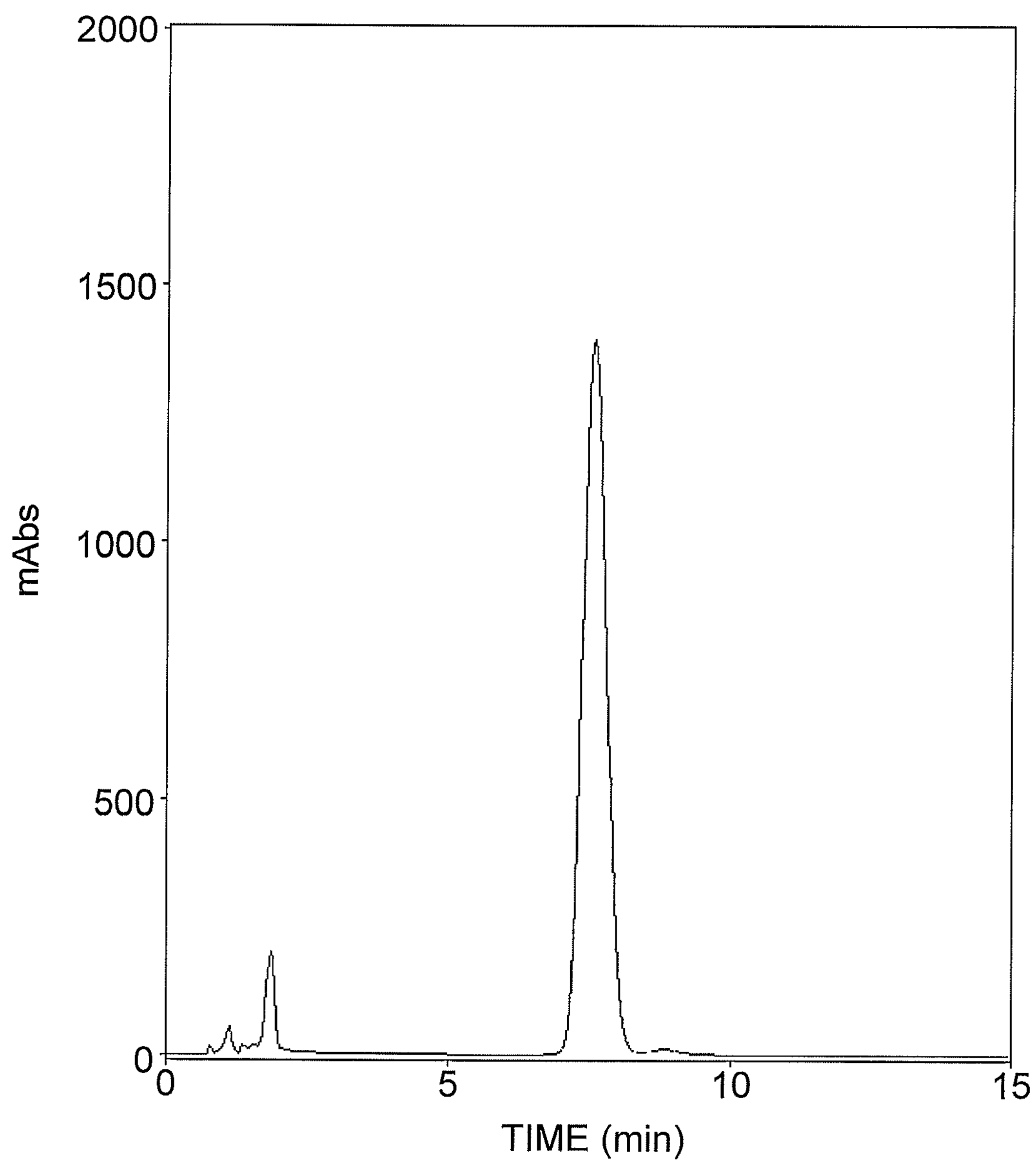
FIG. 3 is an HPLC chart of a microparticle dispersion liquid obtained in Example 1.

FIG. 3 is an HPLC chart of the microparticle dispersion liquid obtained in Example 1. CsA was eluted at a position of approximately 7.5 minutes. The CsA amount in the microparticle dispersion liquid, calculated based on a peak area obtained by measuring the reference preparation, was 9.6 mg/mL. It was thus possible to prepare a microparticle dispersion liquid with an adequately high concentration in comparison to solubility (23 μg/mL) in water. An increase in impurity peaks due to laser light irradiation was not observed on the HPLC chart.

Figure 4:
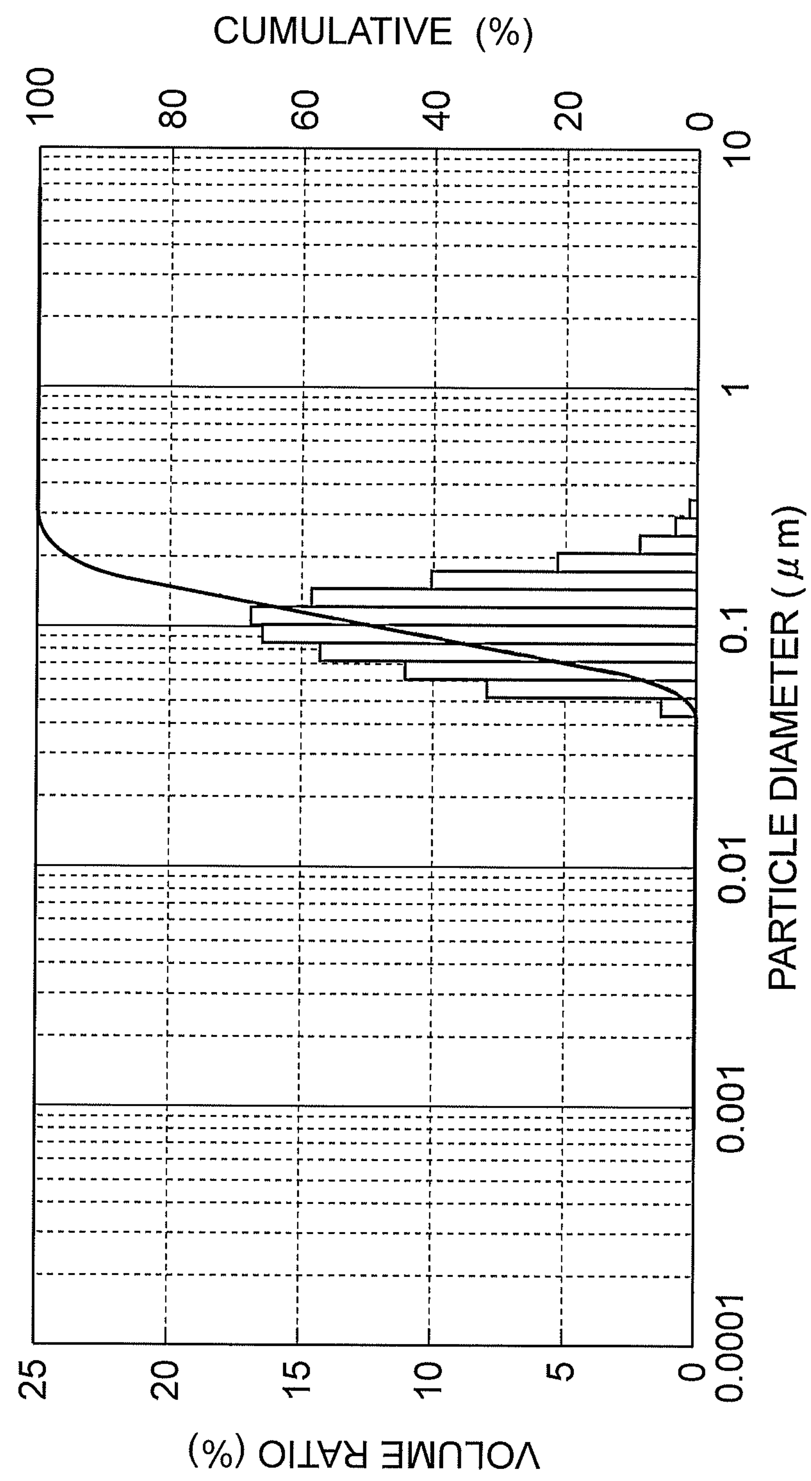
FIG. 4 is a diagram showing a particle diameter distribution of microparticles contained in the microparticle dispersion liquid obtained in Example 1.

FIG. 4 is a diagram showing a particle diameter distribution of microparticles contained in the microparticle dispersion liquid obtained in Example 1. UPA-UT151 (manufactured by NIKKISO CO., LTD.) was used for particle diameter measurement. As can be understood from the figure, presence of microparticles in a particle diameter range of 40 nm to 400 nm was confirmed and the average particle diameter was 109 nm. The microparticle dispersion liquid is thus considered to be that of uniform particle diameter.

Figure 5:
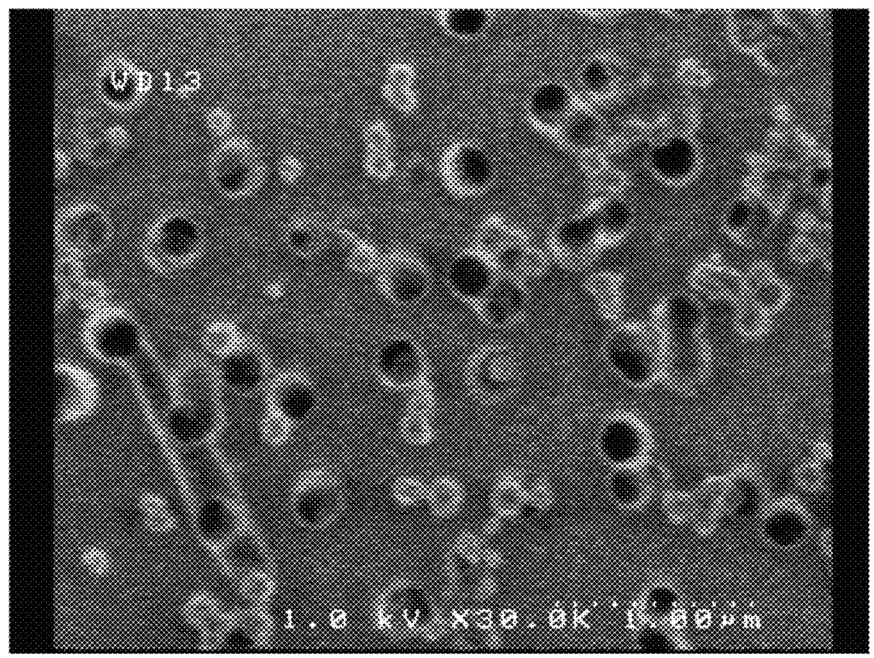
FIG. 5 is an electron micrograph of the microparticles contained in the microparticle dispersion liquid obtained in Example 1.
Figure 8:
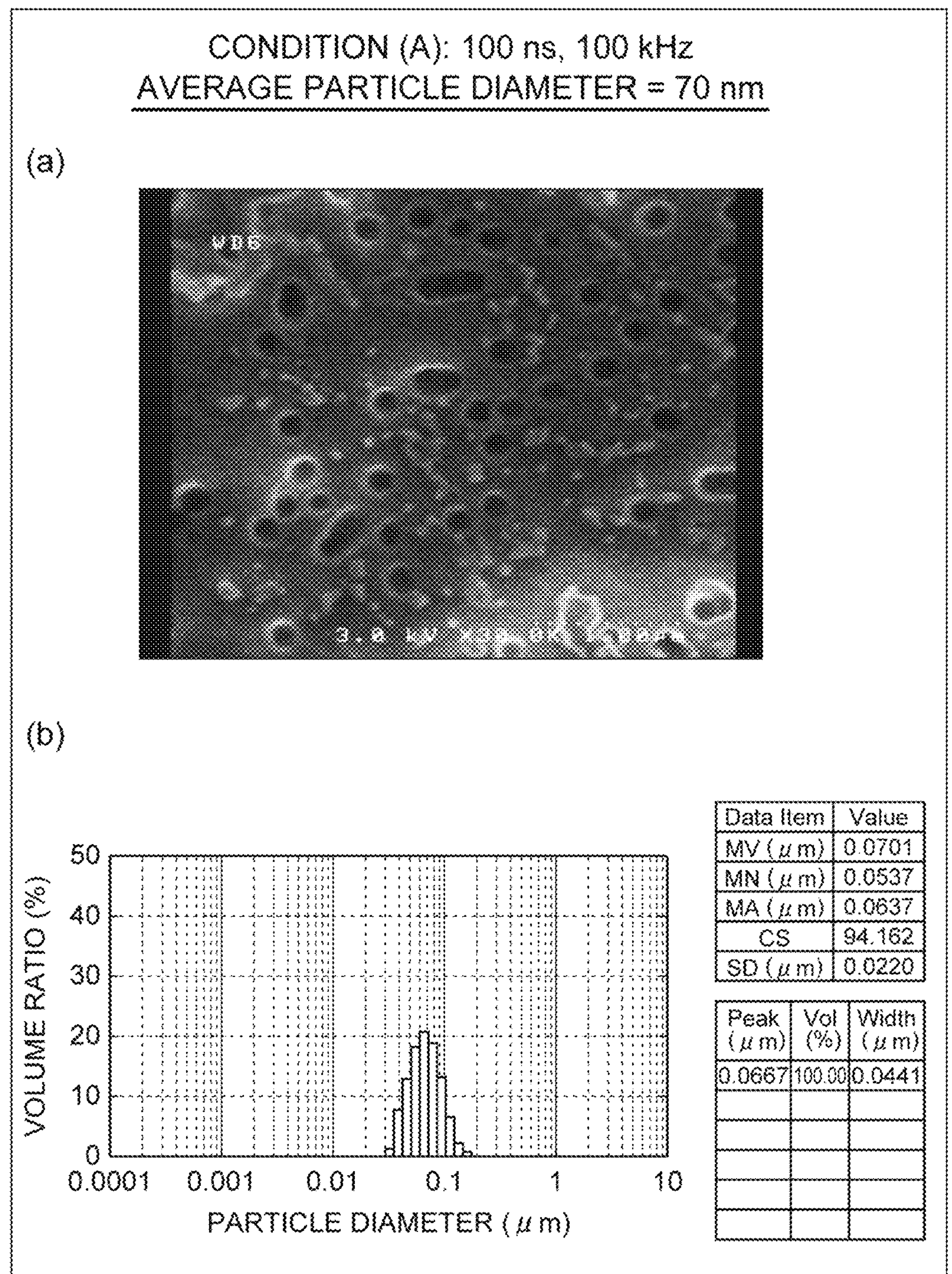
FIG. 8 is a diagram showing an electron micrograph and a particle diameter distribution of microparticles contained in a microparticle dispersion liquid obtained in Example 2.
Figure 9:
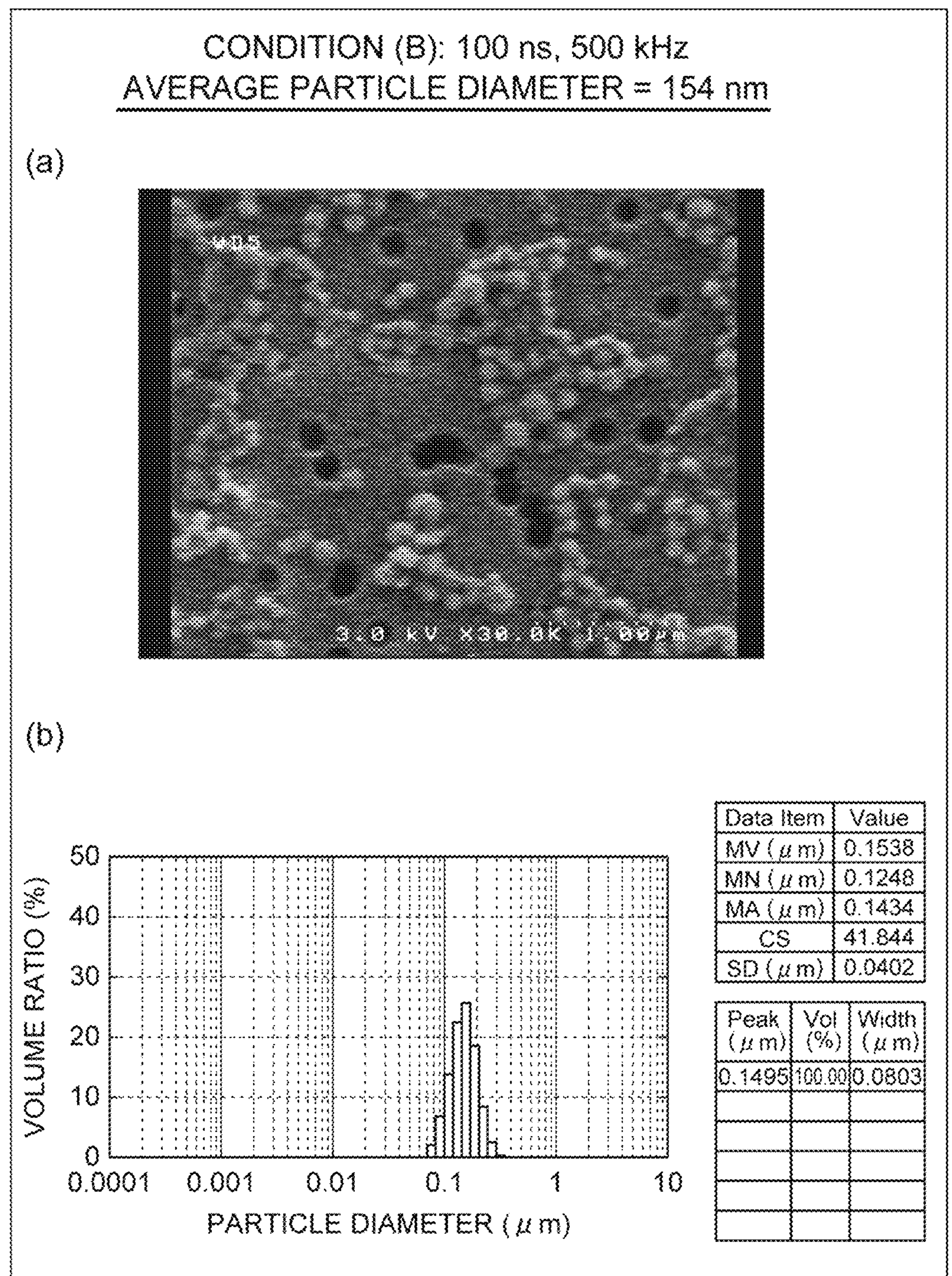
FIG. 9 is a diagram showing an electron micrograph and a particle diameter distribution of microparticles contained in a microparticle dispersion liquid obtained in Example 2.
Figure 10:
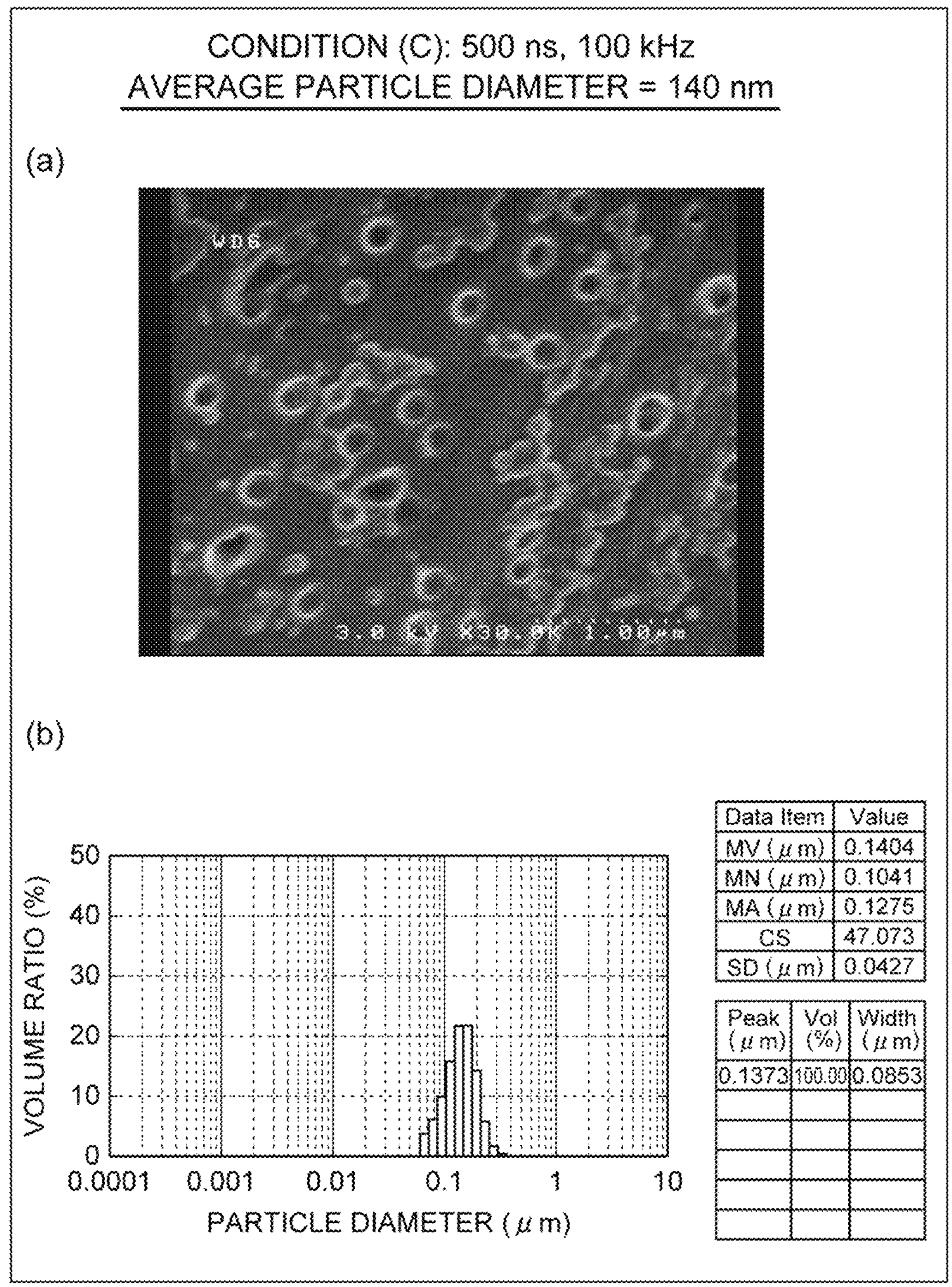
FIG. 10 is a diagram showing an electron micrograph and a particle diameter distribution of microparticles contained in a microparticle dispersion liquid obtained in Example 2.
Figure 11:
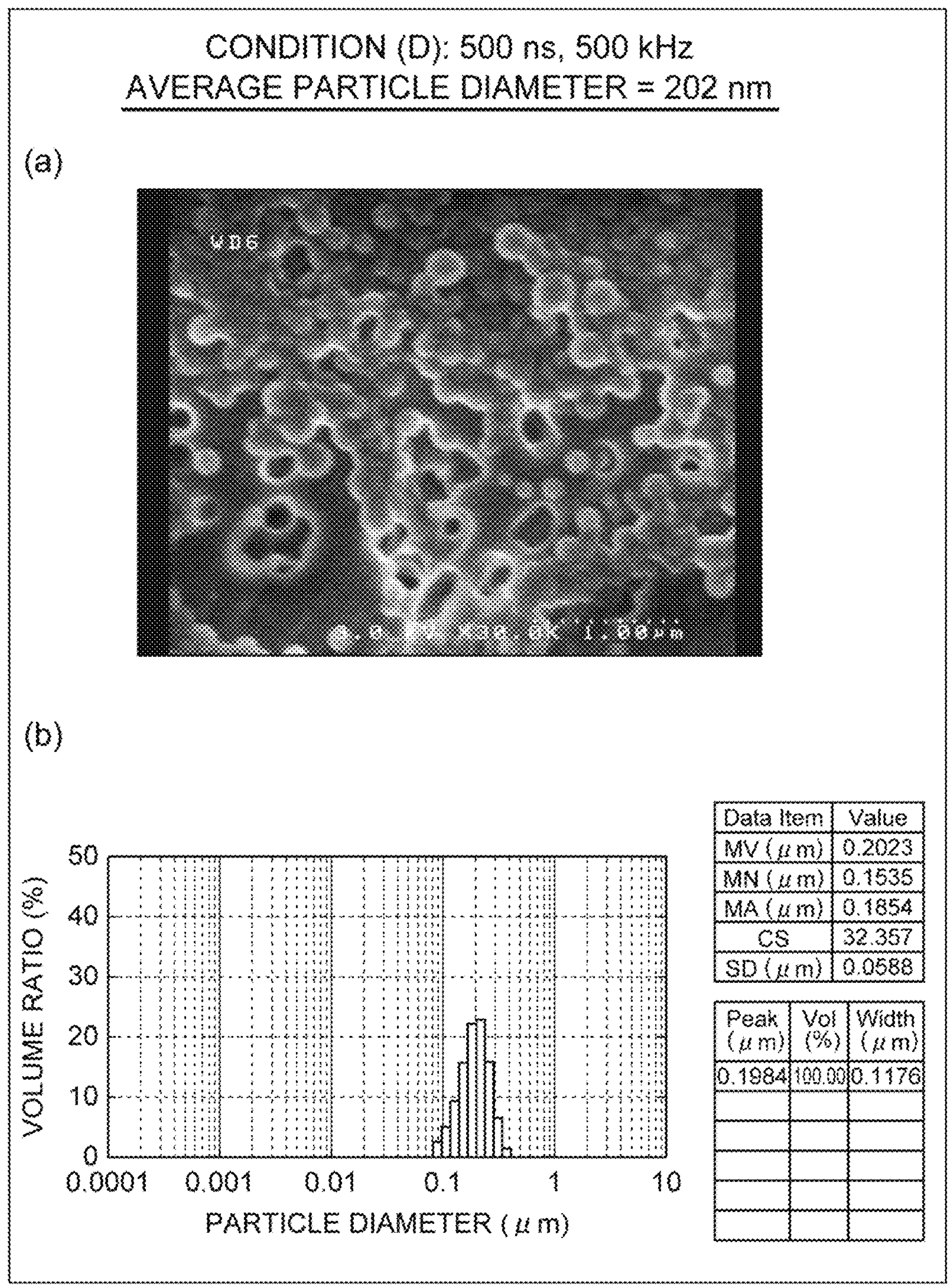
FIG. 11 is a diagram showing an electron micrograph and a particle diameter distribution of microparticles contained in a microparticle dispersion liquid obtained in Example 2.

FIG. 5 is an electron micrograph of the microparticles contained in the microparticle dispersion liquid obtained in Example 1. A scanning electron microscope S4200 (manufactured by Hitachi, Ltd.) was used for photography. Photography was performed after placing the dispersion liquid on a polycarbonate filter of 200 nm pore diameter and drying in air overnight. In the photograph, the pores of the polycarbonate filter appear as black holes and microparticles appear as white objects. As can be understood from the photograph, the microparticles have a spherical shape and numerous microparticles with a particle diameter of approximately 100 nm were observed. This matches the particle size distribution data in FIG. 4, and the microparticles are thus considered as being a uniform assembly of microparticles.

FIG. 6 is a table summarizing success/failure of fine pulverization at various values of amount of water as the solvent injected in each well in Example 1. The amount of water injected as the solvent into each well containing the solid object was varied from 0 mL to 1 mL and pulsed laser light irradiation was performed in each case. Other manufacturing conditions are the same as those described above. In a case where water was not injected at all, the solid object at a vicinity of the light condensed portion became white instantaneously but even when water was injected after the end of irradiation, clouding did not occur. In cases where the water injection amount was 0.1 mL to 0.6 mL, clouding occurred within 1 minute after the start of laser light irradiation. On the other hand, in cases where the water injection amount was no less than 0.7 mL, clouding did not occur even when the laser light was irradiated for no less than 1 minute.

The absorption coefficient of water, used as the solvent 2 in Example 1, is approximately 453 $cm^{-1}$ at the laser light wavelength of 8.6 μm. By calculation, when the laser light of 8.6 μm wavelength is irradiated on a water layer with a thickness of 0.1 mm, the transmitted light is attenuated to $10^{-2}$ with respect to the incident light. Also, when the laser light of 8.6 μm wavelength is irradiated on a water layer with a thickness of 1 mm, the transmitted light is attenuated to $10^{-20}$ with respect to the incident light. Thus, when as in Example 1 described above, water of a thickness of 1 mm is present above the solid object and the laser light of 8.6 μm wavelength is irradiated from above, most of the energy of the laser light is absorbed by the water, the energy of the laser light reaching the solid object is made slight, and photodegradation and thermal degradation of the solid object are suppressed.

(Example 2)

Example 2 shall now be described. In Example 2, a quantum cascade laser light source outputting pulsed laser light of 5.8 μm wavelength was used. FIG. 7 is a table summarizing output conditions of pulsed laser light in Example 2. Irradiation for 10 minutes was performed in accordance with the four types of output conditions of (A), (B), (C), and (D) shown in FIG. 7. Other manufacturing conditions, the particle diameter distribution measurement conditions, and microscope observation conditions are the same as those of Example 1.

Each of FIG. 8 to FIG. 11 is a diagram showing an electron micrograph and a particle diameter distribution of microparticles contained in a microparticle dispersion liquid obtained in Example 2.

In the results for conditions (A) to (D) shown in FIG. 8 to FIG. 11, the average particle diameters are 70 nm, 154 nm, 140 nm, and 202 nm, respectively. As can be understood from the photographs, the microparticles were spherical in shape in all cases. From the particle diameter distribution results, it was considered that the average particle diameter of the microparticles formed increases as the average output of the laser increases.

FIG. 12 is a table summarizing success/failure of fine pulverization at various values of amount of water as a solvent injected in a well under the condition (A) in Example 2 (that is, the conditions of irradiating pulsed laser light of a wavelength of 5.8 μm, pulse width of 100 ns, repetition frequency of 100 kHz, and average output of 31 mW). The amount of water injected as the solvent into each well containing the solid object was varied from 0 mL to 1 mL and pulsed laser light irradiation was performed in each case. Other manufacturing conditions are the same as those described above. In a case where water was not injected at all, the solid object at a vicinity of the light condensed portion became white instantaneously but even when water was injected after the end of irradiation, clouding did not occur. In cases where the water injection amount was 0.1 mL to 0.5 mL, clouding occurred within 1 minute after the start of laser light irradiation. On the other hand, in cases where the water injection amount was no less than 0.6 mL, clouding did not occur even when the laser light was irradiated for no less than 1 minute.

(Example 3)

Figure 13:
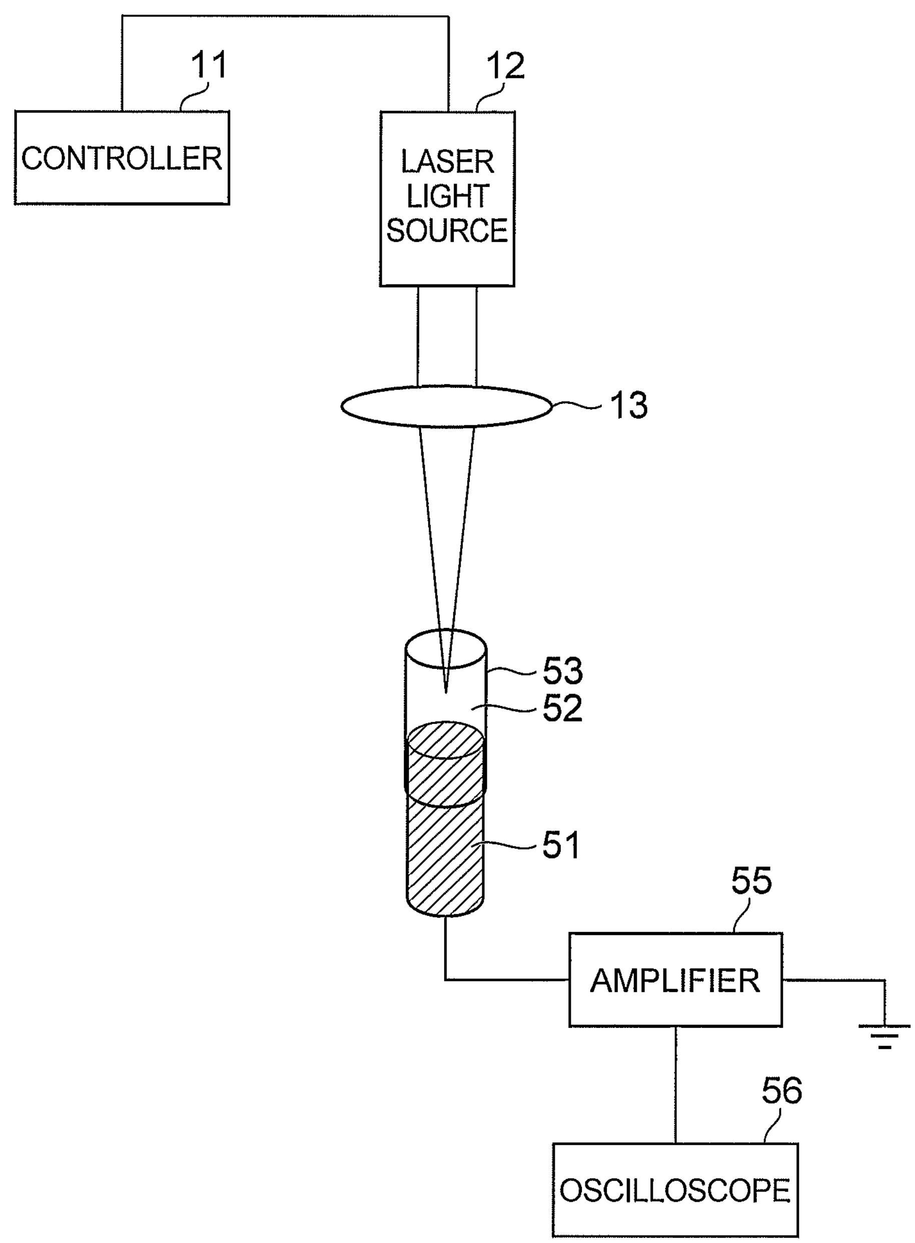
FIG. 13 is a configuration diagram of a pressure wave evaluating apparatus used in Example 3.

Example 3 shall now be described. In Example 3, a pressure wave evaluating apparatus shown in FIG. 13 was used to actually confirm the generation and propagation of the pressure wave in water. A rubber tube 53 was fitted in a closely contacting manner around a commercially available piezoelectric microphone 51 and the microphone 51 was fixed in a vertical direction. An interior of the rubber tube 53 was filled with water 52 and pulsed laser light was condensed near a surface of the water layer. An electromotive force obtained by piezoelectric conversion inside the piezoelectric microphone 51 was amplified by 25 times by an amplifier 55 (dual channel programmable filter 3625, manufactured by NF Corporation) and input into an oscilloscope 56 (digital oscilloscope TDS784A, manufactured by Tektronix Japan) for evaluation.

Figure 14:
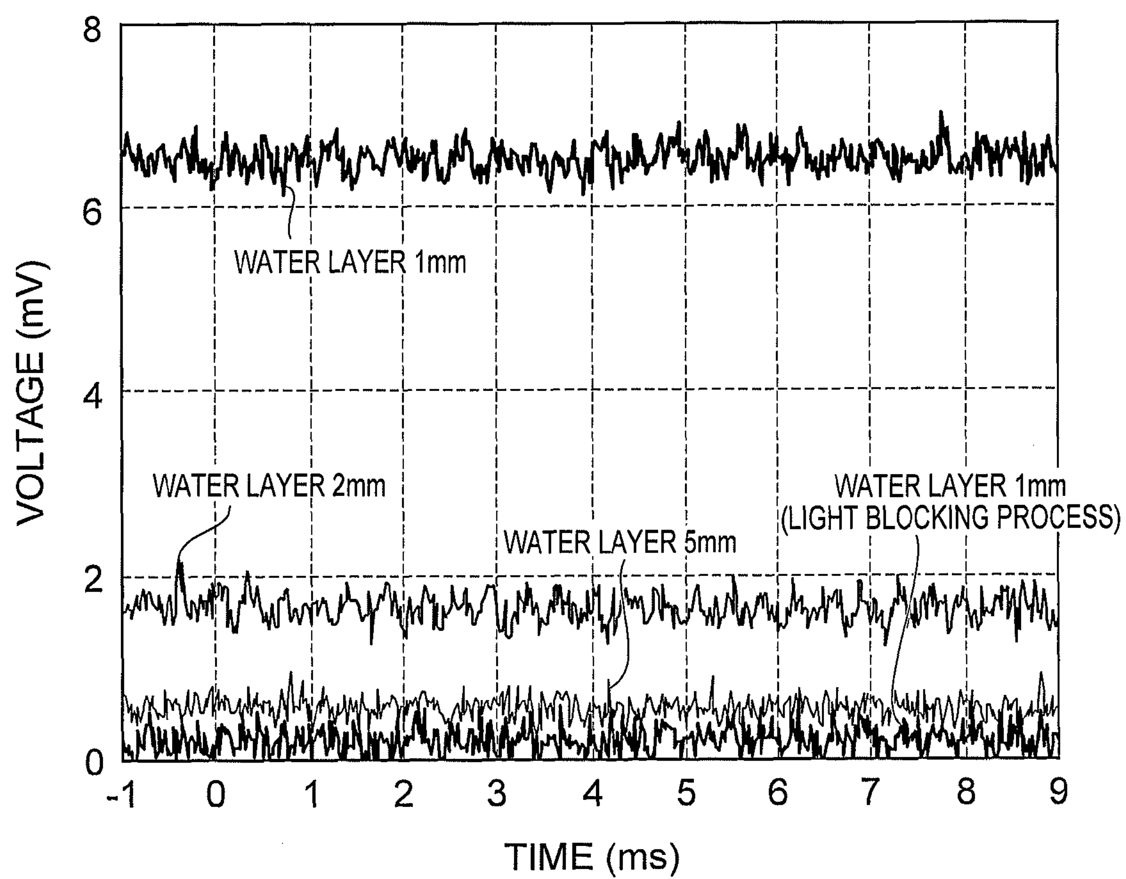
FIG. 14 is a graph showing digital oscilloscope waveforms obtained in Example 3.

FIG. 14 is a graph showing digital oscilloscope waveforms obtained in respective cases where the thickness of the water layer filled inside the rubber tube was set to 1 mm, 2 mm, or 5 mm and pulsed laser light of a wavelength of 5.8 μm, pulse width of 100 ns, repetition frequency of 100 kHz, and average output of 31 mW was irradiated. The graph shows a relationship of the water layer thickness and the electromotive force in a case where the laser output was fixed at 100 ns and 100 kHz. As can be understood from the waveforms, the electromotive force decreases as the water layer thickness is increased and hardly any electromotive force was generated when the thickness became 5 mm. Further, when in the case where the water layer thickness was set to 1 mm, a light blocking object was inserted in the laser light path, an electromotive force was not generated.

Figure 15:
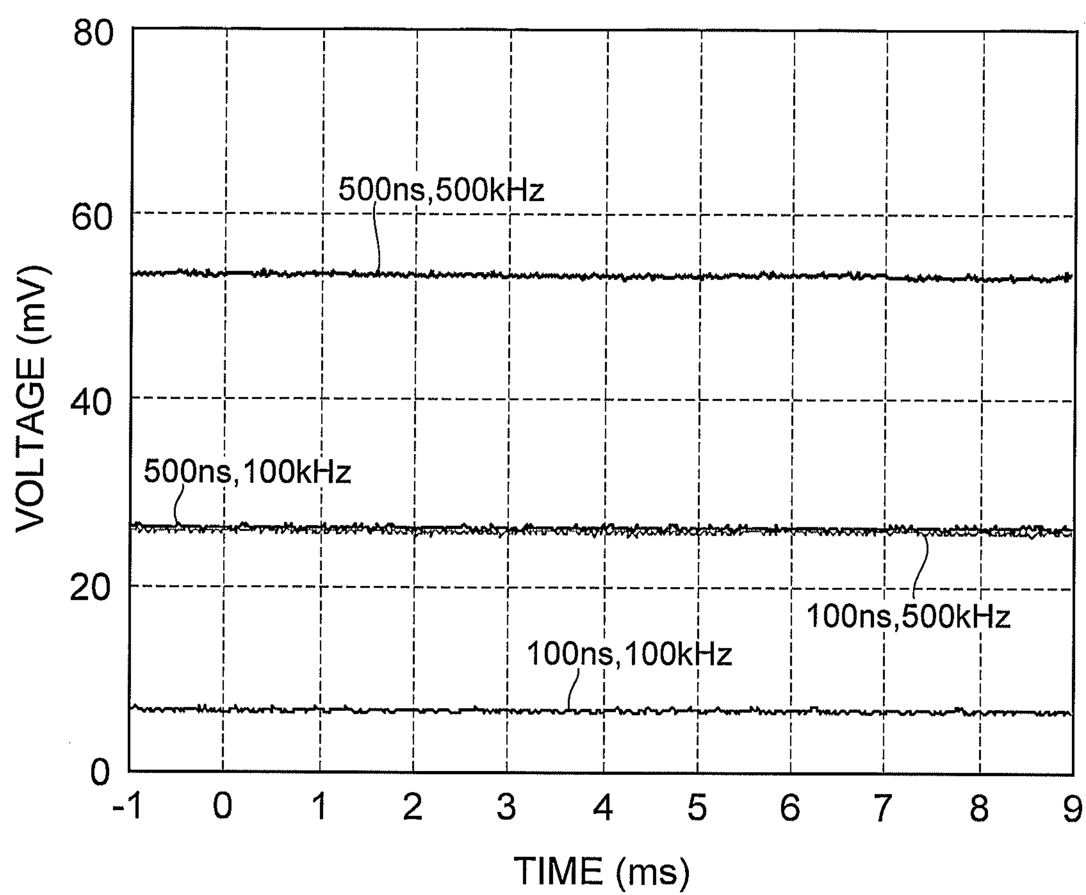
FIG. 15 is a graph showing digital oscilloscope waveforms obtained in Example 3.

Meanwhile, FIG. 15 is a graph showing digital oscilloscope waveforms obtained in respective cases where the thickness of the water layer inside the rubber tube was set to 1 mm and pulsed laser light of a wavelength of 5.8 μm was irradiated at various output conditions. The graph shows a relationship of the laser output and the electromotive force in a case where the water layer thickness is fixed at 1 mm. As can be understood from the waveforms, the electromotive force increases as the average output of the laser is increased.

The absorption coefficient of water, used as the solvent 2 in Example 2 and Example 3, is approximately 715 cm at the laser light wavelength of 5.8 μm. By calculation, when the laser light of 5.8 μm wavelength is irradiated on a water layer with a thickness of 0.1 mm, the transmitted light is attenuated to $10^{-3}$ with respect to the incident light. Also, when the laser light of 5.8 μm wavelength is irradiated on a water layer with a thickness of 1 mm, the transmitted light is attenuated to $10^{-30}$ with respect to the incident light. Thus, when as in Example 2 and Example 3 described above, water of a thickness of 1 mm is present and the laser light of 5.8 μm wavelength is irradiated from above, most of the energy of the laser light is absorbed by the water and the energy of the laser light reaching the solid object is made slight. The energy absorbed by water is consumed for generation of the pressure wave. The pressure wave propagates while being attenuated. When the water layer is made thick, energy of a level that can finely pulverize the solid object does not reach the solid object, and fine pulverization does not occur.

The microparticle dispersion liquid manufacturing method and the microparticle dispersion liquid manufacturing apparatus according to the present invention is not limited to the embodiments and examples described above, and various modifications can be made.

INDUSTRIAL APPLICABILITY

The present invention is applicable as a microparticle dispersion liquid manufacturing method and manufacturing apparatus by which both suppression of impurity formation and an increase in efficiency of microparticle formation can be achieved readily.

REFERENCE SIGNS LIST

1—solid object, 2—solvent, 10—microparticle dispersion liquid manufacturing apparatus, 11—controller, 12—light source, 13—irradiation optical system, 14—container.

The invention claimed is:

1. A microparticle dispersion liquid manufacturing method comprising:

a dissolving step of dissolving a poorly-soluble medicament and a dispersion stabilizer in a volatile organic solvent; and a fixing step of performing elimination by evaporation of the organic solvent, contained in a solution obtained in the dissolving step, and fixing a solid object, obtained by the organic solvent elimination, on an inner wall of a container; and an injecting step of injecting, after the fixing step, a solvent into the container containing the solid object to attain a state where the solvent is present above the solid object and the solid object is in contact with the solvent inside the container; and an irradiating step of performing, after the injecting step, repeated irradiation of the solvent with pulsed light from a top of the solvent side so that most of the energy of the pulsed light is absorbed by the solvent selectively among the solid object and the solvent inside the container to cause expansion and contraction of the solvent to occur repeatedly at the irradiated portion to generate a pressure wave in the solvent and make the pressure wave act on the solid object fixed on the inner wall to finely pulverize the solid object and thereby manufacture a microparticle dispersion liquid in which microparticles are dispersed in the solvent.

2. A microparticle dispersion liquid manufacturing apparatus comprising:

a container, in an interior of which a solid object is contained and a solvent is injected to attain a state where the solvent is present above the solid object and the solid object is in contact with the solvent; and a light source repeatedly irradiating the solvent with pulsed light from a top of the solvent side so that most of the energy of the pulsed light is absorbed by the solvent selectively among the solid object and the solvent inside the container; and wherein the solvent is repeatedly irradiated with the pulsed light from the light source to cause expansion and contraction of the solvent to occur repeatedly at the irradiated portion, thereby generating a pressure wave in the solvent, and the pressure wave is made to act on the solid object fixed on an inner wall to finely pulverize the solid object and thereby manufacture a microparticle dispersion liquid in which microparticles are dispersed in the solvent, and wherein a poorly-soluble medicament and a dispersion stabilizer are dissolved in a volatile organic solvent in the interior of the container, the solid object obtained by elimination by evaporation of the organic solvent contained in the solution is fixed on the inner wall of the container, and the solvent is injected into the interior of the container.

3. The microparticle dispersion liquid manufacturing method according to claim 1, wherein, in the irradiating step, the repeated irradiation of the solvent is performed with the pulsed light selectively from above.

4. The microparticle dispersion liquid manufacturing apparatus according to claim 2, wherein the light source repeatedly irradiates the solvent with the pulsed light selectively from above.

* * * * *